United States Patent
Mueller

(10) Patent No.: US 8,979,531 B2
(45) Date of Patent: Mar. 17, 2015

(54) DOUBLE-ARCHED TWEEZERS FOR DENTAL OPERATIONS

(75) Inventor: Daniel Mueller, Burgstall (IT)

(73) Assignee: Dental Care Innovation GmbH, Nürnberg (DE)

( * ) Notice: Subject to any disclaimer, the term of this patent is extended or adjusted under 35 U.S.C. 154(b) by 0 days.

(21) Appl. No.: 13/817,551

(22) PCT Filed: Aug. 19, 2010

(86) PCT No.: PCT/IB2010/002061
§ 371 (c)(1),
(2), (4) Date: Apr. 29, 2013

(87) PCT Pub. No.: WO2012/022997
PCT Pub. Date: Feb. 23, 2012

(65) Prior Publication Data
US 2013/0224682 A1  Aug. 29, 2013

(51) Int. Cl.
*A61C 3/00* (2006.01)
*A61C 3/10* (2006.01)
*B25B 9/02* (2006.01)

(52) U.S. Cl.
CPC .... *A61C 3/10* (2013.01); *B25B 9/02* (2013.01)
USPC .......................................................... 433/162

(58) Field of Classification Search
USPC ......... 433/3, 4, 141, 159, 162, 163; D24/143;
D28/55; 606/51, 52, 210, 211;
968/665, 666; 294/99.1, 99.2; 30/235,
30/236, 253
See application file for complete search history.

(56) References Cited

U.S. PATENT DOCUMENTS

| 468,746 | A | * | 2/1892 | How | 433/159 |
| 1,626,226 | A | * | 4/1927 | Cantor | 433/159 |
| 1,657,497 | A | * | 1/1928 | Cichon | 294/99.2 |
| 2,030,798 | A | * | 2/1936 | Krajeski | 433/159 |
| 3,866,610 | A | * | 2/1975 | Kletschka | 606/208 |
| 3,972,333 | A | * | 8/1976 | Leveen | 606/174 |
| 4,197,647 | A | * | 4/1980 | Goldenthal | 433/159 |
| 4,226,240 | A | * | 10/1980 | Walker, Jr. | 606/207 |
| 4,226,241 | A | * | 10/1980 | Walker, Jr. | 606/207 |
| 4,827,929 | A | * | 5/1989 | Hodge | 606/139 |
| 5,015,252 | A | * | 5/1991 | Jones | 606/205 |
| 6,095,815 | A | * | 8/2000 | Mueller | 433/159 |
| 6,322,363 | B1 | * | 11/2001 | Beecher et al. | 433/159 |
| 6,699,039 | B2 | * | 3/2004 | Dryer | 433/159 |
| 6,776,616 | B2 | * | 8/2004 | Dryer | 433/159 |

(Continued)

FOREIGN PATENT DOCUMENTS

| DE | 3730348 A1 | * | 3/1989 | A61C 3/10 |
| DE | 19503333 C1 | | 3/1996 | |
| DE | 29808043 U1 | | 9/1998 | |
| DE | 102004032558 A1 | * | 2/2006 | A61C 3/10 |

OTHER PUBLICATIONS

PCT Search Report prepared by the European Patent Office in corresponding PCT/IB2010/002061, May 4, 2011, 4 pages.
International Preliminary Report on Patentability prepared by the European Patent Office in corresponding PCT/IB2010/002061, Feb. 19, 2013, 7 pages.

*Primary Examiner* — Heidi M Eide
*Assistant Examiner* — Matthew Saunders
(74) *Attorney, Agent, or Firm* — Hooker & Habib, P.C.

(57) ABSTRACT

In order to get good access for treatment at hidden parts of the oral cavity, double arched tweezers are disclosed, that can favorably be applied for operations at one or the other side of the mouth and by left- or right-handed dentists.

18 Claims, 4 Drawing Sheets

(56) References Cited

U.S. PATENT DOCUMENTS

| | | | |
|---|---|---|---|
| D516,246 S * | 2/2006 | Lin | D28/55 |
| 2002/0106609 A1 * | 8/2002 | Palermo et al. | 433/159 |
| 2003/0224323 A1 * | 12/2003 | Dryer | 433/153 |
| 2003/0224324 A1 * | 12/2003 | Dryer | 433/153 |
| 2004/0106084 A1 * | 6/2004 | Dryer | 433/159 |
| 2004/0142303 A1 * | 7/2004 | Dryer | 433/153 |
| 2011/0151406 A1 * | 6/2011 | Solano et al. | 433/162 |

* cited by examiner

Fig. 1
Prior Art
Fig. 2
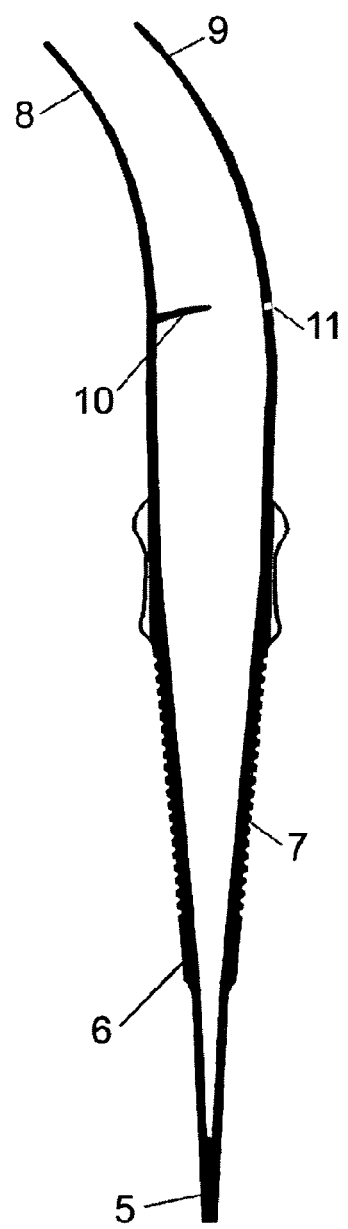
Fig. 3
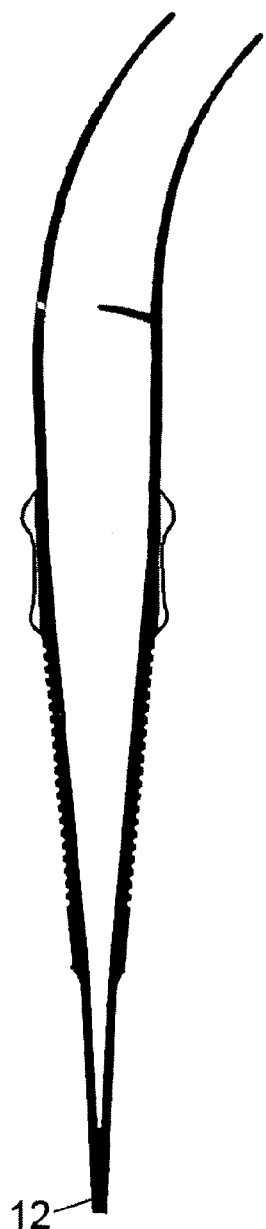

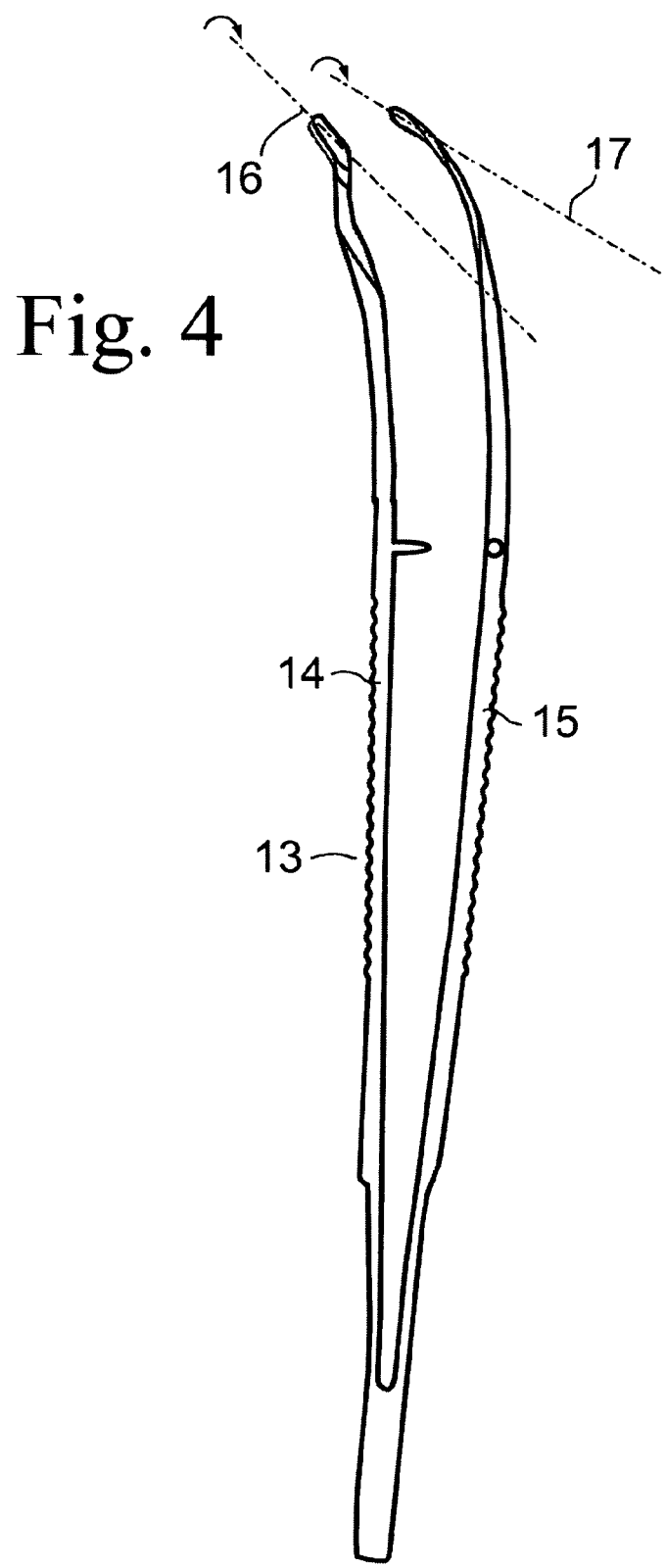

DOUBLE-ARCHED TWEEZERS FOR DENTAL OPERATIONS

FIELD OF THE INVENTION

The invention relates to dental instruments and more particularly to tweezers used for dental operations.

BACKGROUND OF THE INVENTION

The oral cavity offers a spatially quite limited work area for dental treatment, but accessibility of the target area is crucial for the quality of dental operations. However, tools and equipment hitherto available do not always meet the spatial conditions in the oral cavity:

Some most often treated target areas are situated within the range of the palate or, on backside of the tongue, in the lower jaw.

Right and left tooth rows are to be worked on completely differently, but there is only identical equipment offered for both fields.

Moreover, frequently surfaces of teeth are concerned, which are hidden to direct observation, or are within interdental spaces and thus averted to direct sight, or hidden by template strands, tapes or fixing clips, which inhibit direct access to the working area.

Furthermore the working position of the dentist, facing the oral cavity, is but hardly variable. Thus direct access can only rarely be achieved.

Therefore instruments, that can only be used at straight access to the field of work and which inevitably do not consider a widening angle between the field of work and the pinpointing of the instrument resulting from its handhold position, are actually inappropriate.

Problem to be Solved

The problem therefore is to find a way to treat these hidden spaces within the oral cavity, particularly safely to place or remove dabbers and to clear off gingival tissue, as well as correctly placing inlays etc.

PRIOR ART

Surprisingly, there had just a small number of disclosures been found, that relate to this or similar problems. However, there are quite a few intellectual property rights applied for tweezers or forceps of different purposes:

So U.S. Pat. No. 3,971,270 is particularly made for stamps, U.S. Pat. No. 4,240,435, U.S. Pat. No. 4,593,694 and WO 2006/134283 A for depilation, WO 90/15579 for removing ticks, WO 2009/114896 A1 for catching head lice, CN 2187450(Y) for handling ophthalmic lenses, DE 195 03 333 C1 for placing pins or screws and DE 198 08 656 A1 for cosmetic self-treatment.

There even are tweezers disclosed for medical operations, as U.S. Pat. No. 5,007,827, a crossover-type to better hold orthodontic braces, or U.S. Pat. No. 6,776,615 B2, for placing strip- or thread-shaped material, held between rod-shaped clamping elements, blockable holding forceps as in DE 11 2006 003 996 T5, or suspended operational forceps with clamping mechanism, as in CN 201005756(Y)

Furthermore, there are quite a few tweezers disclosed, that are collapsible or foldable, as in U.S. Pat. No. 7,625,028 B2 and in U.S. Pat. No. 7,641,248 B2, which consist of special material or are made with a particular production method, as U.S. Pat. No. 6,916,054 B1, or have a particular deign, as e.g. double ended tweezers in WO 2006/065641 A2, forceps with skin-pull arrangement as in CN 201294953 (Y), levered pincettes in WO 2009/074954 A2, tweezers with limited tip pressure in DE 101 55 585 A1, or with levered action as in DE 196 37 618 A1.

But sofar there seem to be no instrument published or made, for to solve the problem of asymmetrical access to operational areas.

INVENTIVE STEP

Considering the imperfectness of existing medical equipment to this point, the solution came with different tests of modified instruments for shoving away gigival and other tissue of the oral cavity, so to get access to zones to be treated and to get clear sight thereof.

With respect to the problem of asymmetrical approach as to the side to be treated, the position of the operator and his/her left- or right-handedness, the application of instruments with an appropriate left or right arching within the horizontal plane proved to be favorable.

In a further step the combination with tweezers or forceps solved the problem of avoiding the application of more instruments than necessary and to find a solution not only to get access to hidden zones, but simultaneously to be able to exactly place orthodontic utilities and implements there.

SUMMARY OF THE INVENTION

The present invention therefore comprises asymmetrical dental tweezers with a differentiation between instruments applied for left and right side.

In case of tweezers it therefore is necessary to bend not only its tips, but also to angle up the end piece against the handles, so to achieve a differentiation between "right" and "left handling". An angle of approximately 45-60 degrees—with respect to the tweezers grip—therefore turned out to be appropriate.

For to ensure that the legs of these tweezers are travelling adequately to each other when actuated by pressing them together, one of the two arms is carrying a pin with an adjusted light bending, that inserts into—and thus is guided by—a flat hole in the opposite arm.

In another embodiment of the invention the tips of the tweezers may carry rounded, dish-type plates for a better grip at dabbers or fine matrices.

Furthermore these plates, as well as ordinary tips may be covered with crushed diamonds, so to secure a better grip.

Moreover, instead of gripping plates, one of the tips may contain a fine metal clip, under which thin films, as used for separations, may be clamped and transported to their destination.

In a further embodiment the tweezers tips may be modified in a way, that the outer ends of the tips carry a wedge-shaped hypomochlion on both sides with a spacing of 3 to 4 Millimeters. This can be used as interdental lever for many applications.

DESCRIPTION OF THE DRAWINGS

The invention is further disclosed in detail with the following drawings, wherein:

FIG. 1 shows in top view straight tweezers 1 of a basic kind, wherein both tips are forged downwards (not to be recognized on a top view) comprising a straight pin 2 and a guiding hole 3.

Figure 4A:
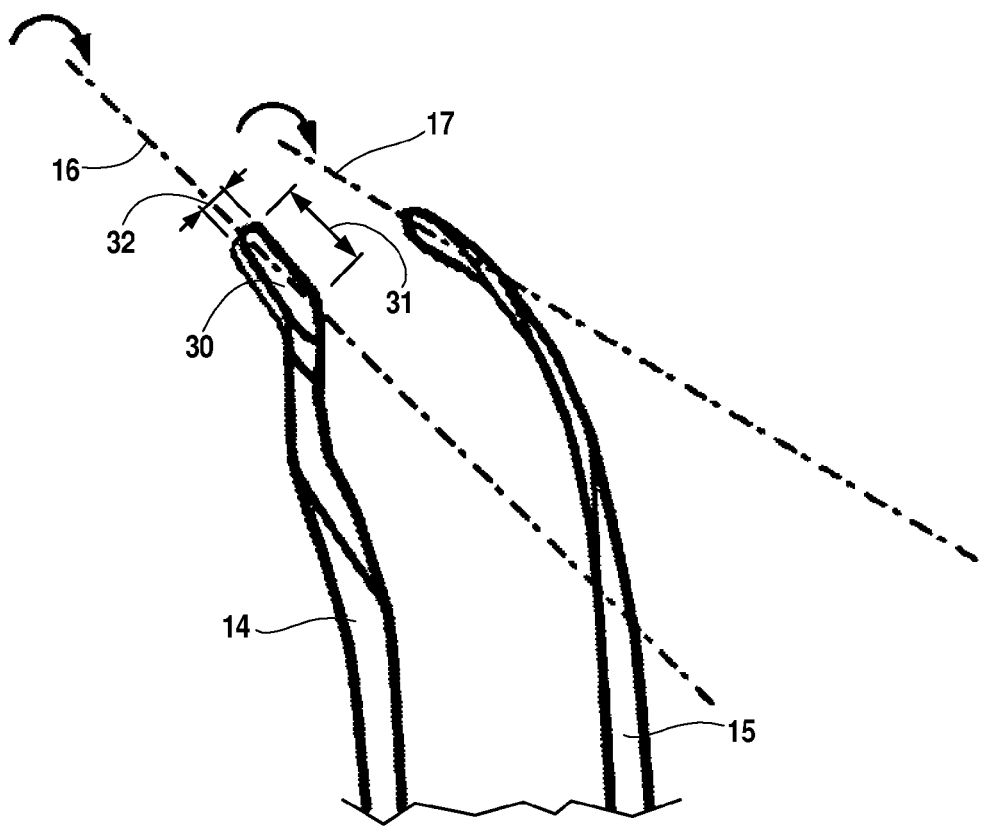

This drawing is only for comparison with FIG. 2 and FIG. 3.

FIG. 2 discloses the left type of asymmetric tweezers 5 in the same top view, where the left arm 6 is bent to the right side, whereas the right arm 7 has a little different bending line, so to achieve exact closing of the tips 8 and 9.

Also for this purpose, the pin 10 on the left arm of these tweezers is also a little bent, for to pass through the guiding hole 11 on the right arm at changing geometrical positions of pin and hole in their movement.

FIG. 3 discloses the right-handed version 12 of the tweezers, built symmetrical to the left handed version in FIG. 2.

FIG. 4 shows a left-handed tweezer 13, the arms 14 and 15 of which are twisted to left side along their axis 16 and 17.

FIG. 4A is an enlarged view of the respective tip portions 18, 19 of the arms 14, 15.

Figure 5:
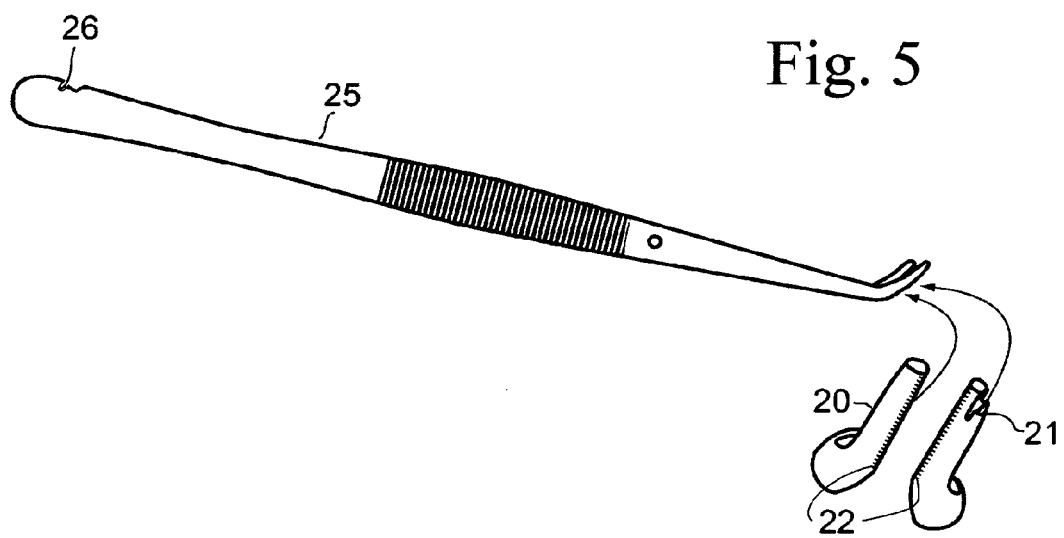

FIG. 5 shows the tweezers 25, wherein a slit 26 forms a miniature clamping device, suited to hold thin films or matrices, that need to be held in place when filling gaps in one tooth to prevent adhesion to a neighbouring one.

An attached detail drawing shows one of the tips 20, comprising a slit 21 for clamping fine threads for operational application within. The tips also include opposing surfaces or holding sides, each surface or side coated with crushed diamonds 22.

The tweezers shown in FIG. 4 has each tip portion extending along the respective tip axis 16, 17 to an end of the arm. The tip axes 16, 17 define a tip plane that, in the illustrated embodiment, is parallel with the drawing sheet as viewed in FIG. 4A.

Each tip portion 18, 19 includes a dish-type plate or gripping surface 30, the gripping surfaces facing each other during normal use of the tweezers in gripping an object. Each gripping surface 30 has a length dimension 31 extending along the tip axis and a width dimension 32 transverse to the tip axis. The length and width dimensions of each gripper surface define a respective gripping plane associated with each gripping surface. As indicated by the arrows in FIG. 4A, each gripping plane is inclined at an acute angle away from the perpendicular with respect to the tip plane—that is, with respect to the illustrated embodiment, the gripping planes are inclined at acute angles away from the perpendicular with respect to the drawing sheet as viewed in FIG. 4A.

What is claimed is:

1. Tweezers or forceps comprising:

a first elongated arm and a second elongated arm; each arm comprising a first end, a second end, an attachment portion at the first end, an elongate handle portion extending from the attachment portion, an elongate curved portion extending from the handle portion, and a tip portion extending from the curved portion along a tip axis to the second end of the arm;

the attachment portions of the first and second arms attached to each other and springingly biasing the first and second arms away from each other to opened positions of the first and second arms, the handle portion and the curved portion of the first arm spaced from and not touching the handle portion and the curved portion of the second arm when the first and second arms are each in the opened position;

the handle portion and the curved portion of each arm extending along a line, the lines of the first and second arms defining a first plane which forms a horizontal plane, the handle and curved portions movable in the horizontal plane toward and away between opened and closed positions from each other for opening and closing the tweezers or forceps;

each tip portion comprising a gripping surface having a length dimension extending parallel with the tip axis and a width dimension extending transverse to the tip axis, the length and width dimensions defining a second plane associated with the tip portion;

the curved portion of the first arm curving away from the second arm as the curved portion of the first arm extends from the handle portion to the tip portion of the first arm;

the curved portion of the second arm curving towards the first arm as the curved portion of the second arm extends from the handle portion to the tip portion of the second arm the tip axes of the tip portions defining a third plane;

and the gripping surfaces generally facing one another with the second planes defined by the gripping surfaces each being inclined at an angle inclined with respect to the third plane.

2. Tweezers or forceps of claim 1 wherein the tip portions of the first and second arms extend away from one side of the horizontal plane as the tip portions extend from the curved portion of the arms to the second ends of the arms.

3. Tweezers or forceps of claim 2 wherein the third plane is parallel with the horizontal plane.

4. Tweezers or forceps of claim 1 wherein the tip portions of the first and second arms each also curve in the horizontal plane as the tip portion extends from the curved portion of the arm to the second end of the arm.

5. Tweezers or forceps of claim 4 wherein the tip portion and the curved portion of each of the first and second arms have the same horizontal curvature where the tip portion extends from the curved portion whereby the tip portion curves smoothly from the attachment portion.

6. Tweezers or forceps of claim 1 wherein at least a portion of the curved portion of each of the first and second arms comprises sides that are twisted about the respective line associated with the arm.

7. Tweezers or forceps of claim 6 wherein the tip portions of the first and second arms extend away from one side of the horizontal plane as the tip portion of each of the first and second arms extend from the curved portion of the arm to the second end of the arm.

8. Tweezers or forceps of claim 1 wherein the curved portion of each arm curves between 45 degrees and 60 degrees from the handle portion of the arm to the tip portion of the arm.

9. Tweezers or forceps of claim 1 comprising a guiding rod extending from the curved portion of one of the first and second arms and a hole in the curved portion of the other of the first and second arms configured and disposed to receive the guiding rod when closing the tweezers or forceps, the guiding rod being bent.

10. Tweezers or forceps of claim 1 wherein each gripping surface is a flat surface.

11. Tweezers or forceps of claim 1 comprising crushed diamonds on said gripping surfaces.

12. Tweezers or forceps of claim 1 wherein one of the first and second arms comprises a fine slit opening into the arm, the slit configured and disposed for forming a clamping fixture for fine threads.

13. Tweezers or forceps of claim 12 wherein the slit is disposed in the tip portion of the one arm and extends into the said tip portion in a direction transverse to the horizontal plane.

14. Tweezers or forceps of claim 13 wherein the slit extends into the tip portion of the one arm in a direction generally parallel with the tip axis of the one arm.

15. Tweezers or forceps of claim 1 wherein the attachment portions of the first and second arms form a butt at the first ends of the arms, a slit extending into the butt from an outer surface of the butt.

16. Tweezers or forceps of claim 15 wherein the slit extends into the butt in a direction transverse to the horizontal plane.

17. Tweezers or forceps of claim 1 wherein the tip axes are not parallel with one another when the tweezers or forceps are in the opened position.

18. Tweezers or forceps of claim 1 wherein the gripping surfaces are located at the second ends of the arms.

\* \* \* \* \*